United States Patent
Wijayaratna et al.

(10) Patent No.: US 10,165,982 B2
(45) Date of Patent: Jan. 1, 2019

(54) PHONE FOR USE IN HEALTH MONITORING

(71) Applicants: SANANDCO LIMITED, Bingham, Nottingham (GB); Claire Wijayaratna, Nottingham (GB)

(72) Inventors: Saneth Wijayaratna, Bingham (GB); Michael Pearson, Effingham (GB)

(73) Assignee: SANANDCO LIMITED, Bingham, Nottingham (GB)

( * ) Notice: Subject to any disclaimer, the term of this patent is extended or adjusted under 35 U.S.C. 154(b) by 141 days.

(21) Appl. No.: 15/119,362

(22) PCT Filed: Feb. 17, 2015

(86) PCT No.: PCT/GB2015/050453
§ 371 (c)(1),
(2) Date: Aug. 16, 2016

(87) PCT Pub. No.: WO2015/121689
PCT Pub. Date: Aug. 20, 2015

(65) Prior Publication Data
US 2017/0055911 A1 Mar. 2, 2017

(30) Foreign Application Priority Data
Feb. 17, 2014 (GB) .................................. 1402728.8

(51) Int. Cl.
*A61B 5/00* (2006.01)
*A61B 5/01* (2006.01)
(Continued)

(52) U.S. Cl.
CPC .......... *A61B 5/6898* (2013.01); *A61B 5/0022* (2013.01); *A61B 5/01* (2013.01);
(Continued)

(58) Field of Classification Search
CPC ... A61B 2562/066; A61B 5/0022; A61B 5/01; A61B 5/0205; A61B 5/02055;
(Continued)

(56) References Cited

U.S. PATENT DOCUMENTS 5,357,427 A  10/1994 Langen et al.
5,931,791 A   8/1999 Saltzstein et al.
(Continued)

FOREIGN PATENT DOCUMENTS

CA  2428250 A1  11/2003
CN  102334977 A   2/2012
(Continued)

OTHER PUBLICATIONS

Extended European Search Report, for European Patent Application No. 17197631.9, dated Dec. 8, 2017, 9 pages.
(Continued)

*Primary Examiner* — George Manuel
(74) *Attorney, Agent, or Firm* — Kinney & Lange, P.A.

(57) ABSTRACT

A phone comprising: a phone body, at least one sensor on the phone body for measuring a vital sign of a user when the phone is held in use; means for converting the vital sign measurement into a voice-frequency band signal; and means for transmitting the voice-frequency band signal for use in monitoring the health of the user.

15 Claims, 6 Drawing Sheets

(51) Int. Cl.
*A61B 5/0205* (2006.01)
*A61B 5/0404* (2006.01)
*A61B 5/145* (2006.01)
*H04M 11/06* (2006.01)
*G06F 19/00* (2018.01)
*G16H 10/60* (2018.01)
*A61B 5/0285* (2006.01)
*A61B 5/08* (2006.01)
*A61B 5/083* (2006.01)

(52) U.S. Cl.
CPC ........ *A61B 5/0205* (2013.01); *A61B 5/02055* (2013.01); *A61B 5/0404* (2013.01); *A61B 5/14542* (2013.01); *A61B 5/7465* (2013.01); *G06F 19/3418* (2013.01); *G16H 10/60* (2018.01); *H04M 11/066* (2013.01); *A61B 5/0285* (2013.01); *A61B 5/0809* (2013.01); *A61B 5/0816* (2013.01); *A61B 5/0836* (2013.01); *A61B 2562/066* (2013.01); *H04M 2250/12* (2013.01)

(58) Field of Classification Search
CPC ... A61B 5/0285; A61B 5/0404; A61B 5/0809; A61B 5/0816; A61B 5/0836; A61B 5/14542; A61B 5/6898; A61B 5/7465; G06F 19/322; G06F 19/3418; H04M 11/066; H04M 2250/12
See application file for complete search history.

(56) References Cited

U.S. PATENT DOCUMENTS

| | | | |
|---|---|---|---|
| 6,219,408 B1 | 4/2001 | Kurth | |
| 6,804,558 B2 * | 10/2004 | Haller | A61N 1/37264 128/903 |
| 8,323,189 B2 * | 12/2012 | Tran | A61B 5/0024 600/300 |
| 2005/0070968 A1 | 3/2005 | Bergelson et al. | |
| 2008/0027340 A1 * | 1/2008 | Kuo | A61B 5/02405 600/509 |
| 2013/0289366 A1 | 10/2013 | Chua et al. | |
| 2015/0335293 A1 * | 11/2015 | Christman | A61B 5/6897 600/324 |

FOREIGN PATENT DOCUMENTS

| | | |
|---|---|---|
| CN | 202128470 U | 2/2012 |
| EP | 2425768 A1 | 3/2012 |
| EP | 2617354 A1 | 7/2013 |
| EP | 002575100-0001 | 11/2014 |
| WO | 97/28736 A1 | 8/1997 |
| WO | 99/04687 A1 | 2/1999 |
| WO | 01/32075 A2 | 5/2001 |
| WO | 2013/157669 A1 | 4/2012 |
| WO | 2014/022906 A1 | 2/2014 |

OTHER PUBLICATIONS

British Office Action dated Aug. 20, 2014 for corresponding Application No. GB1402728.8.
International Search Report and Written Opinion dated May 4, 2015, for corresponding PCT Application No. PCT/GB2015/050453.
Heiko Gesche et al., "Continuous blood pressure measurement by using the pulse transit time: comparison to a cuff-based method", European Journal of Applied Physiology, Published online: May 10, 2011.

* cited by examiner

1050 — Measure vital sign of user when phone held in use

1051 — Convert vital sign measurement into voice-frequency band signal

1052 — Transmit voice-frequency band signal for use in monitoring health of user

PHONE FOR USE IN HEALTH MONITORING

TECHNICAL FIELD

The present disclosure relates to the field of health monitoring, associated apparatus and methods, and in particular concerns a phone configured to measure a vital sign of a user, convert the vital sign measurement into a voice-frequency band signal and transmit the voice-frequency band signal for use in monitoring the health of the user.

BACKGROUND

An ever-increasing ageing population and growing comorbidities has led to an increase in the demand for healthcare. It has become apparent that going to accident and emergency (A&E) and then being admitted to hospital has become the default route for urgent and emergency care. A major problem is the growing proportion of patients attending A&E departments who are being admitted. Ten years ago in the UK it was fewer than one in five. Now it is more than one in four. This not only puts pressure on the medical staff in the A&E department, but also on the National Health Service (NHS) as a whole. It is estimated that at least a fifth of patients admitted as emergencies could be managed outside of hospital.

To try and address this issue, the NHS has introduced a free number for patients with urgent, but not life-threatening symptoms (NHS 111 service). The call centres are manned by trained call handlers. However, reports have emerged of patients facing long waits for advice, and emergency services have being inundated with patients who have been either incorrectly referred by the call handlers or who are simply unable to get any help at all.

By July 2013, there were over half a million calls to the NHS 111 service. Scaled up, this represents over 9 million calls per year across England of which a substantial amount will be referred to some form of urgent care such as an A&E department. Significantly, over 50% of these calls are from patients with long term conditions, and the number of people with long term conditions is set to grow.

It would be desirable to have a device which would allow patients to contact their healthcare provider and alleviate their concerns without putting pressure on the healthcare provider.

It would also be useful to produce a device, such as a phone, which is capable of providing a set of patient observations during a phone consultation in real-time and for use in telehealth applications. In particular, it would be useful to provide a low cost phone to every patient that is likely to use a healthcare service frequently, such as patients who have recently been discharged from hospital.

Smart phones have become increasingly popular with the general public for their diverse abilities such as navigation, social networking, and multimedia facilities to name but a few. These phones are equipped with high end processors, high resolution cameras, built-in sensors like accelerometers, orientation-sensors, light-sensors, and much more. Motivated by the capability of smart phones and their extensive usage, they are being increasingly utilized in the healthcare industry and for bio-medical applications.

However, smart phones are very expensive, and elderly patients often find them overly complicated to use. It would be desirable to produce a cheap alternative phone which is capable of measuring vital signs. Furthermore, smart phones use a wireless or Bluetooth™ connection in order to transmit and receive data, which can be less reliable than fixed phone lines and can cause confusion for users when they fail to connect. It would be useful to send the data through an analogue signal (such as a fixed telephone line) where no wireless or Bluetooth™ connection is required.

The apparatus and methods described herein may address one or more of these issues.

The listing or discussion of a prior-published document or any background in this specification should not necessarily be taken as an acknowledgement that the document or background is part of the state of the art or is common general knowledge.

SUMMARY

According to a first aspect, there is provided a phone comprising:
  a phone body;
  at least one sensor on the phone body for measuring a vital sign of a user when the phone is held in use;
  means for converting the vital sign measurement into a voice-frequency band signal; and
  means for transmitting the voice-frequency band signal for use in monitoring the health of the user.

One or both of the shape and arrangement of the phone may be configured to encourage a left-handed hold over a right-handed hold by the user.

The at least one sensor may comprise an SPO2 sensor positioned in a concave recess on the phone body, and one or both of the concave recess and SPO2 sensor may be arranged on the phone body to encourage the left-handed hold over the right-handed hold.

The concave recess may be formed at least partially on the left side of the phone body.

The centre of the concave recess may be positioned at the centre of the rear side of the phone body, at the centre of the left side of the phone body, or at a location therebetween.

The concave recess may be formed on the rear side of the phone body, and one or both of the concave recess and the SPO2 sensor may be rotationally offset from the longitudinal axis of the phone body.

One or both of the concave recess and the SPO2 sensor may be rotationally offset from the longitudinal axis by 5°-35°.

The concave recess may be formed on the rear side of the phone body and may be tilted towards the left side of the phone body.

The concave recess may be tilted at an angle of up to 30° from an axis normal to the centre of the rear side.

The SPO2 sensor may comprise an emitter configured to illuminate a thumb or finger of the user with light when the thumb/finger is positioned within the concave recess, and a detector configured to detect light from the emitter which has been reflected by the user's thumb/finger.

The phone may be configured to provide an indication when the amount of light detected by the detector of the SPO2 sensor is outside a predefined range.

The concave recess may have a substantially elliptical, rectangular, circular or square shape.

One or both of the size and shape of the phone body may be configured to enable the phone to be held with a prehensile grip.

The phone body may have a generally elongated shape.

The phone body may have a substantially circular, elliptical, square or rectangular cross-section.

The phone body may have a generally curved or C-shaped longtudinal axis.

One or both of the size and shape of the phone body may be configured to allow the user's fingers to be positioned between the phone and the user's cheek when the phone is held in use.

The at least one sensor may comprise a first ECG electrode positioned on the rear side of the phone body such that the electrode contacts the palm of the user's hand when the phone is held in use.

The phone may be configured to provide an indication when there is insufficient contact between the first ECG electrode and the palm of the user's hand when the phone is held in use.

The at least one sensor may comprise a second ECG electrode positioned on the earpiece of the phone such that the electrode contacts the ear of the user during use.

One or both of the first and second ECG electrodes may have a generally convex shape to facilitate contact with the palm or ear of the user, respectively.

The at least one sensor may comprise a temperature sensor positioned on the earpiece of the phone such that it faces the ear cavity of the user during use.

The second ECG electrode may have an annular configuration, and the temperature sensor may be positioned at the centre of the earpiece and encircled by the second ECG electrode.

The phone may be configured to provide an indication when the temperature measured by the temperature sensor is outside a predefined range.

The phone body may comprise front and rear surfaces configured to form an edge of the phone where they meet one another.

The front and rear surfaces maybe configured to meet one another at an angle of no more than 90°.

The at least one sensor may comprise metal on it exterior surface.

The phone body may comprise one or more markers configured to guide the positioning of the user's hand during use of the phone.

The one or more markers may comprise at least one of lights, textured regions, coloured regions and demarcations.

The one or more markers may comprise the emitter of an SPO2 sensor.

The phone may comprise an earth electrode positioned on the rear side of the phone body such that the electrode contacts the palm of the user's hand when the phone is held in use, the earth electrode configured to ground the user prior to measurement of the vital sign by the first and second ECG electrodes.

The at least one sensor may comprise an ECG sensor and an SPO2 sensor, and the phone may be configured to determine blood pressure based on electrocardiography and photoplethysmography measurements obtained using the respective ECG and SPO2 sensors.

The voice-frequency band signal may be a dual-tone multi-frequency signal.

The phone may be configured to measure the vital sign, convert the vital sign measurement into a voice-frequency band signal and/or transmit the voice-frequency band signal in real-time in response to a request from an operator or automated system.

The phone may comprise a button on the phone body configured to initiate measurement of the vital sign.

The means for transmitting may be configured to transmit the voice-frequency band signal via a telephone network or the internet.

The means for transmitting may be configured to transmit the voice-frequency band signal to a remote location for use in remote monitoring of the user's health.

The means for transmitting may be configured to transmit the voice-frequency band signal to a health record.

The phone may comprise means for receiving data stored on the health record.

The at least one sensor may be configured to measure one or more of the following vital signs: heart rate, heart regularity, oxygen saturation, blood pressure and temperature.

The at least one sensor may comprise one or more of an ECG sensor, an SPO2 sensor, a temperature sensor and a pulse sensor.

According to a further aspect, there is provided a method of using any phone described herein, the method comprising:
    measuring a vital sign of a user when the phone is held in use;
    converting the vital sign measurement into a voice-frequency band signal; and
    transmitting the voice-frequency band signal for use in monitoring the health of the user.

According to a further aspect, there is provided a phone comprising:
    a phone body;
    at least one sensor on the phone body for measuring a vital sign of a user when the phone is held in use; and
    means for transmitting the vital sign measurement for use in monitoring the health of the user.

The means for transmitting may or may not be configured to transmit the vital sign measurement as a voice-frequency band signal.

The means for transmitting may be configured to transmit the vital sign measurement via one or more of a telephone, internet, WiFi™ or Bluetooth™ connection.

The phone according to the present aspect may comprise any of the features associated with the phone according to the first aspect.

According to a further aspect, there is provided a method of using any phone described herein, the method comprising:
    measuring a vital sign of a user when the phone is held in use; and
    transmitting the vital sign measurement for use in monitoring the health of the user.

According to a further aspect, there is provided a phone comprising:
    a phone body;
    ECG and SPO2 sensors on the phone body for respectively taking electrocardiography and photoplethysmography measurements from a user when the phone is held in use;
    means for determining the blood pressure of the user based on the electrocardiography and photoplethysmography measurements taken using the respective ECG and SPO2 sensors; and
    means for transmitting the determined blood pressure for use in monitoring the health of the user.

The means for transmitting may or may not be configured to transmit the determined blood pressure as a voice-frequency band signal.

The means for transmitting may be configured to transmit the determined blood pressure via one or more of a telephone, internet, WiFi™ or Bluetooth™ connection.

The phone according to the present aspect may comprise any of the features associated with the phone according to the first aspect.

According to a further aspect, there is provided a method of using any phone described herein, the method comprising:
taking electrocardiography and photoplethysmography measurements from a user when the phone is held in use;
determining the blood pressure of the user based on the electrocardiography and photoplethysmography measurements; and
transmitting the determined blood pressure for use in monitoring the health of the user.

According to a further aspect, there is provided a phone comprising:
a phone body;
ECG and SPO2 sensors on the phone body for respectively taking electrocardiography and photoplethysmography measurements from a user when the phone is held in use; and
means for transmitting the electrocardiography and photoplethysmography measurements taken using the respective ECG and SPO2 sensors for use in determining the blood pressure of the user.

The means for transmitting may or may not be configured to transmit the electrocardiography and photoplethysmography measurements as a voice-frequency band signal.

The means for transmitting may be configured to transmit the electrocardiography and photoplethysmography measurements via one or more of a telephone, internet, WiFi™ or Bluetooth™ connection.

The phone according to the present aspect may comprise any of the features associated with the phone according to the first aspect.

According to a further aspect, there is provided a method of using any phone described herein, the method comprising:
taking electrocardiography and photoplethysmography measurements from a user when the phone is held in use; and
transmitting the electrocardiography and photoplethysmography measurements for use in determining the blood pressure of the user.

According to a further aspect, there is provided a phone comprising:
at least one sensor for measuring a vital sign;
means for converting the sensed vital sign into a voice-frequency band signal; and
means for transmitting the voice-frequency band signal.

The sensor may form part of the phone body and may be selected from a finger pulse sensor, ECG sensor, peak flow sensor, BP finger sensor or an infra-red sensor.

The sensor may be connected directly through the audio port of the phone and may be selected from an SP02 sensor, ECG electrodes, a peak flow sensor or a temperature probe.

The vital sign may be selected from heart rate, blood pressure, temperature, pulse wave transit time, respiratory rate, oxygen saturation and pupil size.

The phone may be disposable.

The voice-frequency band signal may be a dual-tone multi-frequency signal.

The means for converting the sensed vital sign into a voice-frequency band signal may be a processor.

The phone may further comprise a memory for storing a measured vital sign and/or a voice-frequency band signal.

The vital sign data may be stored on the phone as a code.

The phone may further comprise a button, and a user may press the button to record the measurement of the vital sign.

The phone may further comprise a USB dock for upload of a measured vital sign.

The phone may further comprise a display.

The phone may further comprise a graphical user interface.

The phone may comprise a power supply, and the power supply may be a battery.

According to a further aspect, there is provided a method of measuring a vital sign comprising:
measuring a vital sign using any phone described herein;
converting the measured vital sign into a voice-frequency band signal; and
transmitting the voice-frequency band signal.

The voice-frequency band signal may be a dual-tone multi-frequency signal.

The measured vital sign may be transmitted to, and recorded in, a health record in a cloud-based network.

The measured vital sign may be stored on the phone as a code.

The measured vital sign may be transmitted when the data is requested by an automated system, and the automated system may be a cloud-based network.

According to a further aspect, there is provided a kit comprising:
any phone described herein;
an additional sensor; and
optionally a USB dock for upload of data.

The additional sensor may be selected from an SP02 sensor, ECG electrodes, a peak flow meter or a temperature probe.

The steps of any method disclosed herein do not have to be performed in the exact order disclosed, unless explicitly stated or understood by the skilled person.

Corresponding computer programs (which may or may not be recorded on a carrier) for implementing one or more of the methods disclosed herein are also within the present disclosure and encompassed by one or more of the described example embodiments.

The present disclosure includes one or more corresponding aspects, example embodiments or features in isolation or in various combinations whether or not specifically stated (including claimed) in that combination or in isolation. Corresponding means for performing one or more of the discussed functions are also within the present disclosure.

The above summary is intended to be merely exemplary and non-limiting.

BRIEF DESCRIPTION OF THE FIGURES

A description is now given, by way of example only, with reference to the accompanying drawings, in which:—

FIG. 4b illustrates schematically a left-hand side view of the phone of FIG. 4a;

FIG. 4c illustrates schematically a right-hand side view of the phone of FIG. 4a;

FIG. 4d illustrates schematically a cross-sectional view of the phone of FIG. 4a;

FIG. 6a illustrates schematically a user's left thumb positioned over the sensor of FIG. 4a;

FIG. 6b illustrates schematically a user's right thumb positioned over the sensor of FIG. 4a;

DESCRIPTION OF SPECIFIC ASPECTS/EMBODIMENTS

Figure 1:
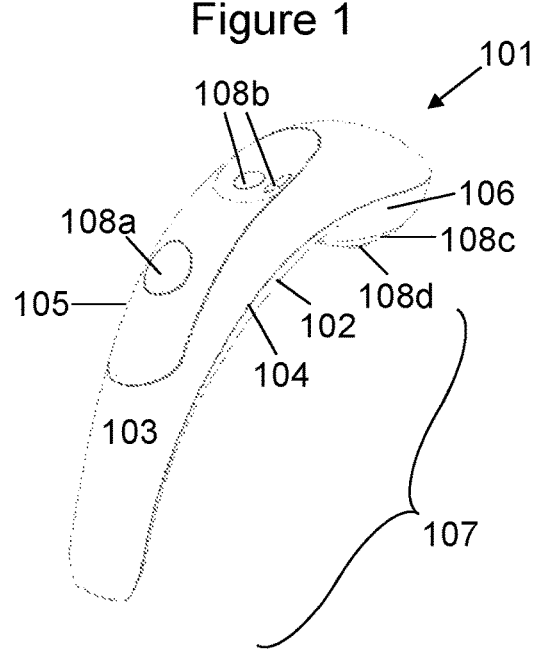
FIG. 1 illustrates schematically one example of a phone described herein.

Later examples depicted in the figures have been provided with reference numerals that correspond to similar features of earlier described examples. For example, feature number 901 can also correspond to feature number 101, etc. These numbered features may appear in the figures but may not be directly referred to within the description of these particular examples. This has been done to aid understanding, particularly in relation to the features of similar earlier described examples.

It is becoming increasingly important that health providers can release patients which have undergone treatment quickly from hospital, as doing so releases beds for other patients. For many medical conditions, the clinician requires ongoing monitoring of the patient in case complications occur. These complications may appear as infection, inflammation, adverse reactions to drugs or other side effects.

The only way a patient can be discharged at present is if the health provider is able to deliver regular nurse visits, or if they choose to use one of a number of telehealth devices. Each nurse visit represents significant cost to the health provider, and whilst these visits may suit certain vulnerable patients, it is less relevant for those who may have a carer or family member to look after them at home. In addition, current telehealth devices tend to suffer from common problems: they are expensive for the health provider, require installation, need significant user training, and often fail in use. As a result they have not been widely adopted by health providers and therefore do not offer a solution to this problem.

Studies have shown that a good way to have an overview of patient health is through the monitoring of a patient's vital signs. Vital signs are vital measurements of physiological statistics and are widely used by healthcare institutions. The primary four vital signs are as follows:

Pulse—the pulse is the physical expansion of the artery. It is equivalent to measuring heart rate.

Blood pressure—blood pressure is the pressure exerted by circulating blood upon the walls of blood vessels. High blood pressure or hypertension affects the kidneys, arteries, heart or endocrine system. Low blood pressure or hypotension can lead to serious heart, endocrine or neurological disorders. In addition, severely low blood pressure can cause shock.

Respirations—respiration rate, or breathing frequency, is the number of breaths taken within a set amount of time, typically 60 seconds. It helps to diagnose an abnormal state of lung. Tachypnea or rapid breathing can be caused by carbon monoxide poisoning, haemothorax or pneumothorax. Dyspnea or shortness of breathing is caused by asthma, pneumonia, cardiac ischemia, interstitial lung disease, congestive heart failure or chronic obstructive pulmonary disease.

Temperature—fever or high temperature can be a symptom for infectious disease, immunological diseases, skin inflammations, tissue destruction, and cancers. Hypothermia or low temperature's risk factors are chronic disease, hypoglycaemia and trauma.

Other vital sign test measurements which can also be performed include:

Pulse oximetry—a simple, relatively cheap and non-invasive technique used to monitor oxygenation by monitoring the percentage of haemoglobin that is oxygen-saturated. Oxygen saturation should always be above 95%, but in those with long-standing respiratory disease or cyanotic congenital heart disease, it may be lower depending on the disease severity. Pulse oximetry is therefore used to detect hypoxemia, and can be advantageous in any setting where a patient's oxygenation is unstable.

Peak flow—the peak expiratory flow, also called peak expiratory flow rate, is a person's maximum speed of expiration. This is typically measured with a peak flow meter; a small, hand-held device used to monitor a person's ability to breathe out air. It measures the airflow through the bronchi and thus the degree of obstruction in the airways.

ECG—an electrocardiogram is a test that checks for problems with the electrical activity of the heart. The wave is analysed for abnormalities such as atrial fibrillation and risk of heart failure.

Studies have also shown that patients would like to be able to monitor their vital signs using a device which is simple, unobtrusive and less invasive. They would also prefer to use a device which does not suffer from installation and connectivity issues. It is also desirable for the patient to be provided with a cheap device from their health care provider which would allow them to upload to, or consult, their own health record, rather than having to buy a personal device which may be expensive.

There will now be described an apparatus and associated methods which may address one or more of these issues. The present disclosure aims to provide a low cost communication device, such as a phone, which is capable of measuring vital signs. An object of the present disclosure is to reduce the number of unplanned admissions to hospitals through enhanced self-care and early interventions via routine monitoring of vital signs. A further object of the present disclosure is to reduce the number of accident and emergency admissions via out of hours and the NHS 111 service through access to real-time vital sign data.

FIG. 1 shows one example of a phone according to the present disclosure. The phone 101 may be a landline (hard-wired or cordless) or mobile phone and comprises a phone body having front 102, rear 103, left 104 and right 105 sides. The phone body defines an earpiece 106, and a handle 107 for the user to grip when using the phone 101. In this example, the phone body has a generally elongated shape with a substantially elliptical cross-section and a generally curved or C-shaped longitudinal axis. In other examples, the phone body may be substantially circular, square or rectangular in cross-section. Although the human hand varies in size and proportion, the dimensions of the phone 101 may be chosen such that the device can be used by as many people as possible. This may be achieved by basing the dimensions of the phone 101 on the average size and shape of a human hand, or by producing a range of phones each having dimensions suitable for a different size and shape of hand (e.g. small, medium and large).

The phone 101 further comprises at least one sensor 108a-d on the phone body for measuring a vital sign of a user when the phone 101 is held in use. In this way, the phone 101 can be used to provide a set of patient observations for baseline monitoring during a remote consultation. Furthermore, provision of the at least one sensor 108a-d on the phone body avoids the need to attach sensors to the user and therefore simplifies the process. In some examples, however, the phone 101 may be configured for connection to one or more detachable sensors (either instead of, or in addition to, the at least one sensor 108a-d on the phone body). In these examples, the one or more sensors may be connected to the phone 101 through a universal audio port in the phone body. This feature allows the number of sensors 108a-d, and therefore the number of vital signs that can be measured by the phone 101, to be increased. In cases where the phone 101 comprises more than one sensor 108a-d, multiple vital signs may be measured sequentially or simultaneously.

The at least one sensor 108a-d may be configured to measure one or more of heart rate, heart regularity, oxygen saturation, blood pressure and temperature. In this respect, the at least one sensor may comprise one or more of an ECG sensor/electrodes 108a,c, an SPO2 sensor 108b, a temperature sensor/probe 108d and a pulse sensor. Furthermore, the one or more detachable sensors may comprise any of the above-mentioned sensors, a cuff-based blood pressure sensor/monitor for measuring blood pressure, a peak flow sensor/meter for measuring peak expiratory flow rate, and/or a respiratory sensor for measuring respiratory rate (e.g. an optical breath, impedance pneumograph or capnograph sensor). In addition, the detection mechanism of the integrated or detachable sensors may be electronic based, optical-based, infrared-based or biochip-based.

The phone 101 may be configured to determine blood pressure based on electrocardiography (ECG) and photoplethysmography (PPG) measurements obtained using respective ECG 108a,c and SPO2 108b sensors. In PPG, the change in volume caused by the pressure pulse is detected by illuminating the skin with light from a light-emitting diode and then measuring the amount of light transmitted or reflected to a photodiode. Each cardiac cycle appears as a peak in the photoplethysmograph. Since blood flow to the skin can be modulated by several other physiological systems, the PPG can also be used to monitor breathing, hypovolemia and other circulatory conditions.

Figure 12:
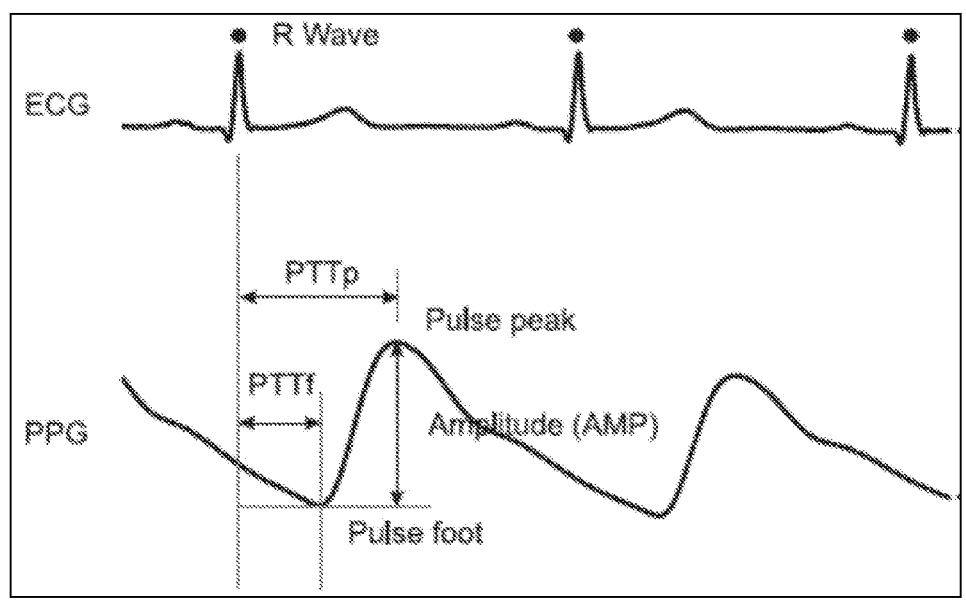
FIG. 12 illustrates graphically the determination of pulse transit time from ECG and PPG measurements.

FIG. 12 shows example ECG and PPG measurements taken by respective ECG and SPO2 sensors. Blood pressure may be determined using the pulse transit time (PTT) obtained from the ECG and PPG measurements. As illustrated in this figure, the PTT is the interval between ventricular electrical activity and peripheral pulse wave. It is calculated from the R-wave of the electrocardiograph (representing ventricular contraction and start of ejection) to the mid-point or top of the rise of the pulse wave in the plethysmograph. This time is related to the pulse wave velocity (PWV), which itself is proportional to the blood pressure.

The PWV (in cm/ms) can be determined from the PTT (in ms) using the following equation:

$$BWV = (BDC \times \text{height})/PTT \qquad \text{Equation 1}$$

where BDC is the body correlation factor and h is the height of the person (in cm). The BDC is the length of the middle of the chest to the finger tips (i.e. half the length of the body) and is typically 0.5 for an adult. Together the BDC and height define the distance that the pulse wave has travelled.

As the blood travels along the artery, it causes expansion of the elastic arterial walls. The physiological reason for the elastic nature of the arterial wall is to buffer the ejection of blood from the heart and to provide a constant flow to the capillary beds. The PWV therefore describes the state of the artery, as defined in Equation 2:

$$PWV = \sqrt{(Eh/\rho D)} \qquad \text{Equation 2}$$

H. Gesche et al demonstrated one method of converting PWV into blood pressure in their paper "*Continuous blood pressure measurement by using the pulse transit time: comparison to a cuff-based method*", Eur J Appl Physiol, 112, No. 1, 309 (2012). In this paper, the authors created a function between systolic blood pressure (SBP) and PWV and tested its reliability for the determination of absolute SBP using a non-linear algorithm and a one-point calibration.

In the study, data from 13 of 53 volunteers served for the detection of a PWV-SBP relationship. At the same time, the SBP was measured using a traditional blood pressure cuff. The difference between the calculated and measured SBP was used in the one-point calibration, and the relation between the calculated and measured SBP was examined using linear regression analysis to determine correlation coefficients.

The resulting non-linear function was then used to calculate SBP values in a group of 50 volunteers. With this, the following empiric mathematical function was derived to fit the PWV and SBP obtained from the 13 selected volunteers:

$$BP_{PTT} = P1 \times PWV \times e^{(P3 \times PWV)} + P2 \times PWV^{P4} - (BP_{PTT,cal} - BP_{cal}) \qquad \text{Equation 3}$$

where $BP_{PTT}$ is the absolute SBP, $BP_{PTT,cal}$ is the calculated SBP, $BP_{cal}$ is the measured SBP and P1-P4 are parameters estimated by least square fitting of the function to the data of the 13 selected volunteer (P1=700, P2=766,000, P3=−1 and P4=9). As can be seen, Equation 3 comprises an exponential term, a second non-linear term and a correction constant (which is the difference between the calculated and measured SBP).

This study shows that the SBP calculated from the PTT using a one-point calibration correlates significantly with the SBP measured by the cuff method. The same (or a similar) approach may be used in the phone described herein. In one scenario, the phone may be configured to determine one or more of the PTT, PWV and blood pressure from the ECG and PPG measurements. In another scenario, the phone may be configured to transmit the ECG and PPG measurements (with or without the PTT and PWV) for use in determining the blood pressure. In the latter scenario, the data may be transmitted to a remote server.

Furthermore, the phone may initially be provided with a detachable blood pressure cuff for measurement of the user's blood pressure. In this way, a database of PTT (or PWV) against blood pressure can be established, which can then be analysed to define appropriate parameters for Equation 3 (or an alternative function). An algorithm can then be defined which will enable the phone or remote server to provide a clinically accurate blood pressure assessment without the use of a blood pressure cuff. Over time, the parameters (and therefore algorithm) may be updated as new blood pressure measurements become available.

In one example, the phone 101 comprises an infrared sensor 108d configured to take a temperature measurement from the user. In this scenario, the infrared sensor may be positioned in the ear piece 106 of the phone 101 to take a temperature reading from the user's temple or inside the user's ear. Additionally or alternatively, the infrared sensor 108d may be positioned on the handle 107 of the phone 101 to take a temperature reading from the user's hand or cheek.

In another example, the phone 101 comprises a finger pulse sensor 108b configured to measure the user's heart rate. In this scenario, the finger pulse sensor 108b may be positioned on the handle 107 of the phone 101 such that the user places his/her index finger over the sensor during use of the phone 101. The finger pulse sensor 108b may also function as a pulse oximeter configured to indirectly monitor the oxygen saturation of the user's blood (as opposed to measuring oxygen saturation directly through a blood sample) and changes in blood volume within the skin.

In yet another example, the phone 101 comprises one or more ECG sensor electrodes 108a,c configured to measure the rate and regularity of the user's heartbeat. The ECG electrodes 108a,c would typically be positioned on the handle 107 and/or earpiece 106 such that they contact the user's hand or ear during use of the phone 101.

The phone 101 also comprises means for converting the vital sign measurements into a voice-frequency band signal, and means for transmitting the voice-frequency band signal for use in monitoring the health of the user. The means for converting the vital sign measurements may comprise a processor (possibly in conjunction with memory and computer program code), or it may comprise suitable logic circuitry. In addition, the means for transmitting the voice-frequency band signal may comprise a transmitter or transceiver configured to transmit the signal via a wired and/or wireless telephone network.

A voice-frequency band is one of the frequencies within part of the audio range that is used for the transmission of speech, and in telephony, ranges from approximately 300 Hz to 3400 Hz. In some examples, the voice-frequency band signal is a dual-tone multi-frequency signal. Dual-tone multi-frequency signalling (DTMF) is used for telecommunication signalling over analogue telephone lines in the voice-frequency band between phone handsets and other communication devices. It is also known commercially as Touch-Tone™ and is used in the majority of phones worldwide. DTMF communicates the numbers dialed to the network by transmitting an assigned frequency to each number. The frequency emitted when a number is dialed creates an audible tone.

Many interactive voice response (IVR) systems today also rely on DTMF tones to route calls when connected. The system at the other end interprets this sound and does the necessary action, such as dialing a phone number, activating a voice command or accessing a menu. IVR allows patients to interact with a host system (such as a system belonging to a healthcare provider) via a telephone keypad or by speech recognition, after which they can service their own inquiries by following the IVR dialogue. IVR systems can respond with pre-recorded or dynamically generated audio to further direct users on how to proceed. They can be used to control almost any function where the interface can be broken down into a series of simple interactions, and are typically sized to handle large call volumes.

Figure 2:
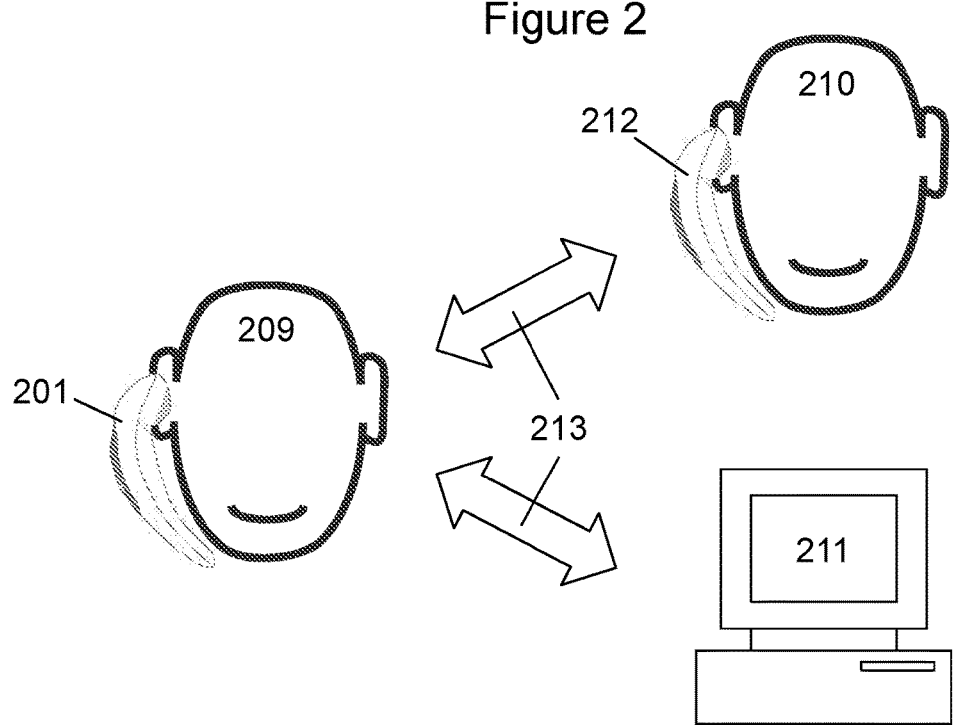
FIG. 2 illustrates schematically a method of measuring a vital sign using a phone described herein.

FIG. 2 shows the phone 201 of FIG. 1 being used to transmit the voice-frequency band signal 213 to a remote location for use in remote monitoring of the user's 209 health. The phone 201 also has the ability to make and receive calls (and may be able to send and receive messages and emails) over a telephone network or the internet. In this way, the phone 201 can be used to transmit the voice-frequency band signal 213 to a health service operator 210 (who may be a clinician) or an automated system/voice prompt 211 (such as a computer comprising IVR software) during a phone call. Either the operator's phone 212 or the IVR-based computer 211 may be configured to convert the voice-frequency band signal 213 back into the original vital sign measurement.

In some cases, the phone 201 may also be able to switch between the telephone call to the operator 210 and the automated system 211 in real-time. This allows the operator 210 to provide help and guidance to the user 209 to assist him/her in providing the vital sign measurement to the automated system 211. In other cases, the voice-frequency band signal 213 may be transmitted from the user 209 to the operator 210 and then on to a computer 211 (e.g. for storage of the vital sign measurement in a patient health record). As well as, or instead of, storing the vital sign measurement for later use, the operator 210 or automated system 211 may analyse the measurements and provide the user 209 with feedback in real-time.

The phone 201 may be configured to measure the vital sign, convert the vital sign measurement into a voice-frequency band signal 213 and/or transmit the voice-frequency band signal 213 in real-time in response to a request from an operator 210 or automated system 211. On the other hand, the phone 201 could be configured to store one or both of the vital sign measurement and the corresponding voice-frequency band signal 213 locally for later transmission. The phone 201 may also comprise an initiation button on the phone body which can be pressed by the user 210 to initiate measurement of the vital sign. Therefore, when the user 209 desires to measure the vital sign, or is instructed to do so by the operator 210 or automated system 211, he/she can press the initiation button to trigger the measurement (and possibly also the conversion and transmission of the reading).

As mentioned above, the phone 201 may be configured to convert the vital sign measurement into a DTMF signal. In practice, this would involve converting the vital sign measurement into a numeric or alphanumeric code for transmission as a series of touch tones. The use of numeric codes also allows a plurality of vital sign measurements to be combined and transmitted as a single code. For example, blood pressure, SPO2 and temperature readings could be converted to the code #121#120.90#456#95#679#37.5#, where #121# is the code for blood pressure and the character string #121#120.90# is the code for a blood pressure reading of 120/90; #456 is the code for SPO2 and the character string #456#95# is the code for an SPO2 reading of 95; #679 is the code for temperature and the character string #679#37.5# is the code for a temperature reading of 37.5° C. Following conversion of the vital sign measurements into the above numeric code, the phone 201 could then dial the number #121#120.90#456#95#679#37.5# in order to transmit the code as a series of corresponding touch tones (which may occur automatically once the user presses the initiation button on the phone body).

Once the DTMF signal has been transmitted, a device 211, 212 at the receiving end would translate the series of touch tones back into the corresponding numeric code and then convert said code back into the original vital sign measurements. The vital sign measurements may then be stored in the relevant sections of a patient health record. The phone 201 may also comprise means for accessing data stored on the patient health record. For example, the user 209 may be able to call an automated system 211 supporting IVR to access previously stored vital sign measurements as well as any other medical data, such as results or feedback.

In some examples, the patient health record itself may be stored in a cloud-based network. The term "cloud" generally refers to a plurality of computers/servers connected to one another through a communication network such as the internet. In the present case, the cloud may be an "e-health cloud" which allows dispersed medical centers, healthcare professionals and their patients to coordinate and exchange information with one another more efficiently. In this way, the user 209 can access his/her medical data via a call to the above-mentioned automated system 211 or via the internet. If the user 209 wishes to store or access data in the e-health cloud via the automated system 211, he/she will typically require a unique number to identify themselves before any data can be transmitted or received. Similarly, the user 209 will typically require a unique username and/or password in order to store or access data in the e-health cloud via the internet.

The e-health cloud may be operated on a pay-as-you-use model to help the healthcare industry cope with current and future demand whilst managing costs. Under this model, clinicians could request vital sign measurements by asking an operator 210 or automated system 211 to call the user/patient 209. The vital sign measurements can then be uploaded to the patient health record and the call can be charged to the healthcare provider (such as a national health service). Additionally or alternatively, the user/patient 209 could call the operator 210 or automated system 211 to provide the vital sign measurements. In this scenario, the call would be charged to the user/patient 209. This flexibility means that the healthcare provider only pays for what it uses rather than paying a fixed monthly or annual communication charge, as is currently common. A further possibility is to sell the phone under a license model.

In order for the present phone 201 to be effective and reliable, the way in which the vital signs are measured should be consistent over time so that accuracy is maintained and any patterns or changes can be detected. In this respect, it has been found that measurements taken by existing handheld systems can vary considerably depending on how the device is held by the user. For example, variations can result from holding the device in different hands, applying different degrees of pressure to a sensor and movement of the user during the measurement. This prevents a meaningful comparison between different datasets and reduces a clinician's ability to trust the results. In addition, such inconsistency in the data also prompts a technician to visit the patient to check the equipment, and if necessary, retrain the patient in the correct use of the device. This adds to the cost of a remote monitoring service and makes it less likely that a healthcare provider will offer such a service over an extended period in hospital.

The phone described herein comprises a number of features to help ensure that it is held in substantially the same manner each time it is used. These features enable more reliable and repeatable measurements than are currently possible with existing home monitoring systems. This means that data trends can be better observed, both from data data associated with each vital sign and also from relationships between data associated with different vital signs. In turn, this allows clinicians to intervene before a patient's symptoms become acute and require emergency treatment.

Figure 3:
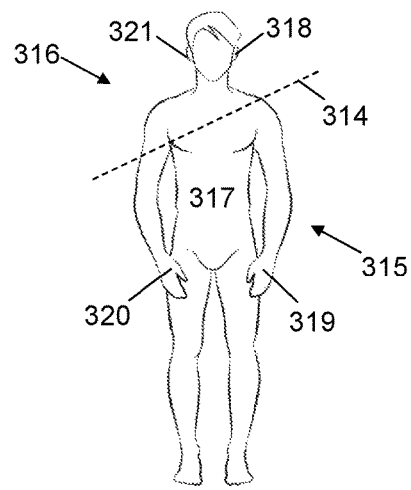
FIG. 3 illustrates schematically the electrical potential line which crosses the human body.

FIG. 3 illustrates the electrical potential line 314 that divides the left 315 and right 316 sides of the human body 317. As can be seen, this line 314 crosses the body 317 at about 30° to the horizontal passing above the heart and dividing the left shoulder from the neck. It has been found that reliable ECG measurements are obtained when the phone comprises respective ECG electrodes on the handle and earpiece, and the phone is held to the left ear 318 by the left hand 319. This is because in this scenario, one ECG electrode is in contact with the left hand 319 (located on one side 315 of the electrical potential line 314), and the other ECG electrode is in contact with the left ear 318 (located on the opposite side 316 of the electrical potential line 314). In contrast, with a right-handed hold, one ECG electrode is in contact with the right hand 320 (located on one side 316 of the electrical potential line 314), and the other ECG electrode is in contact with the right ear 321 (located on the same side 316 of the electrical potential line 314), which inhibits the ECG reading. The use of a left-handed hold also frees up the right hand 320 of the user for other tasks (such as note taking), which is the dominant hand for about 90% of the population.

Due to the advantages provided by a left-handed hold, one or both of the shape and arrangement of the phone described herein may be configured to encourage a left-handed hold over a right-handed hold by the user. This can be achieved in a number of different ways, some of which will now be described.

Figure 4A:
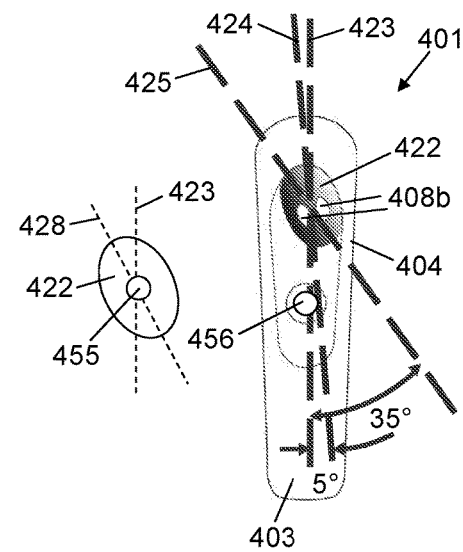
FIG. 4a illustrates schematically one example of a phone described herein comprising a rotationally offset sensor tilted towards the left side of the phone body (rear view)

FIG. 4a shows a rear view of a phone 401 comprising an SPO2 sensor 408b positioned in a concave recess 422 on the rear side 403 of the phone body. The longitudinal 423 and orthogonal 456 axes of the phone body, and the longitudinal 428 and orthogonal 455 axes of the recess 422, are indicated. The concave recess 422 is substantially elliptical, but it could be substantially rectangular, circular or square in shape. In addition, both the concave recess 422 and the SPO2 sensor 408b are arranged on the phone body to facilitate a left-handed hold whilst making a right-handed hold ergonomically difficult and uncomfortable for the user.

This is achieved first of all by rotationally offsetting the concave recess 422 (and SPO2 sensor 408b) from the longitudinal axis 423 of the phone body. In this example, the longitudinal axis 428 of the recess 422 is offset by around 20° from the longitudinal axis 423 of the phone body by rotation of the recess 422 about its orthogonal axis 455, but it could be offset by an angle of anywhere between 5° and 35° (as indicated by the axes 424, 425) and still be suitable for use. Secondly, the concave recess 422 is tilted towards the left side 404 of the phone body by rotation of the recess 422 about its longitudinal axis 428 (as indicated by the shading). In this example, the orthogonal axis 455 of the concave recess 422 is oriented at an angle of around 15° with respect to the orthogonal axis 456 of the phone body, but it could be oriented at any angle up to about 30°. An alternative option (not shown) would be to form the concave recess 422 at least partially on the left side 404 of the phone body by rotation of the recess 422 about the longitudinal axis 423 of the phone body. In other words, rather than the center of the concave recess 422 being positioned at the center of the rear side 403 of the phone body in the width direction (as shown in FIG. 4a), the center of the concave recess 422 may be positioned at the center of the left side 404 of the phone body or at a location between these two points.

Figure 4B:
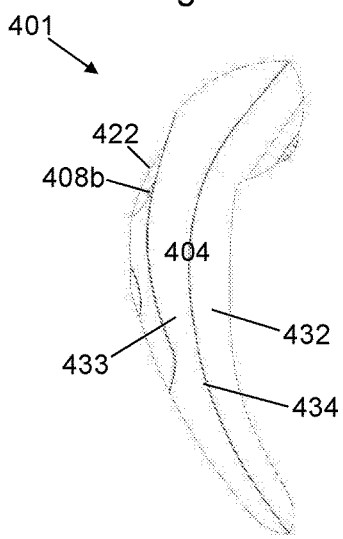
Figure 4C:
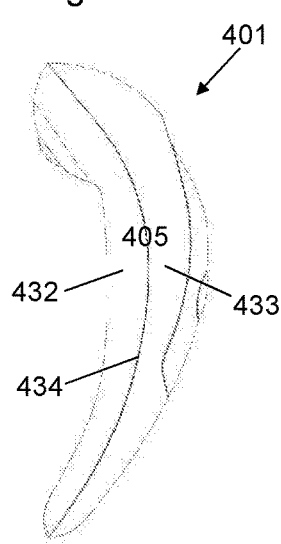
Figure 4D:
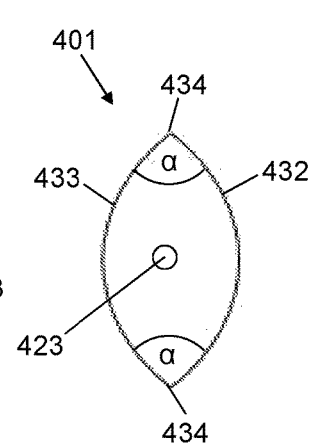

FIGS. 4b, 4c and 4d show the phone 401 of FIG. 4a from the left-hand side 404, right-hand 405 side and in cross-section, respectively. Due to the tilt of the concave recess 422, the surface of the recess 422 can be seen in FIG. 4b but not in FIG. 4c. More importantly, the in-plane rotational offset and out-of-plane tilt make it difficult for the user to fit his/her right thumb fully into the recess 422 to interact with the SPO2 sensor 408b when the phone 401 is held in the right hand.

Figure 5A:
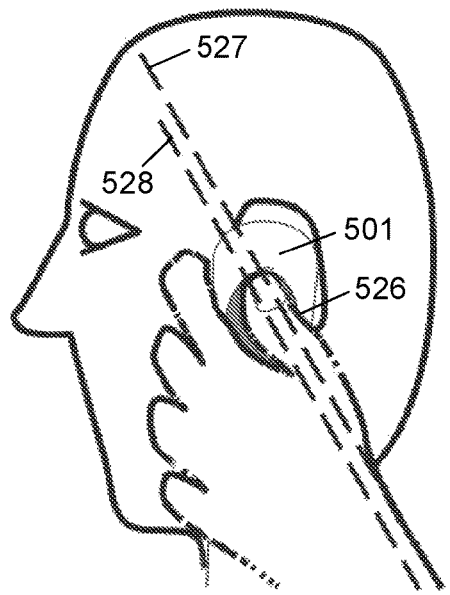
FIG. 5a illustrates schematically a user holding the phone of FIG. 4a in his/her left hand.
Figure 5B:
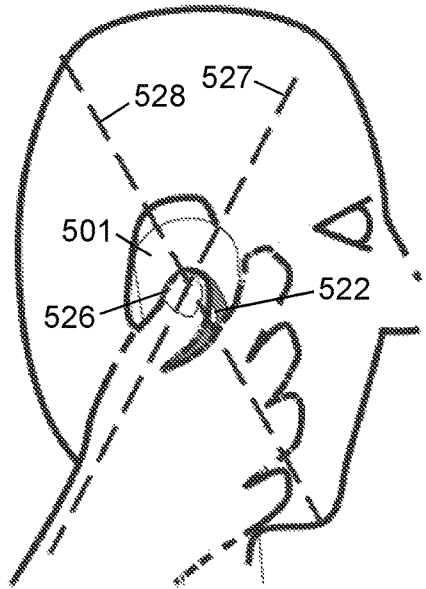
FIG. 5b illustrates schematically a user holding the phone of FIG. 4a in his/her right hand.

FIGS. 5a and 5b illustrate the phone 501 of FIGS. 4a-c in a left-handed hold and a right-handed hold, respectively. The user's thumb 526 can only fit fully into the recess 522 if the longitudinal axis 527 of the thumb 526 is able to align with the longitudinal axis 528 of the recess 522. This is readily possible when the phone 501 is held in the left hand (as shown in FIG. 5a), but is more difficult when the phone 501 is held in the right hand (as shown in FIG. 5b). In the example shown in FIG. 5b, the longitudinal axis 527 of the user's thumb 526 is almost perpendicular to the longitudinal axis 528 of the concave recess 522.

Figure 6A:
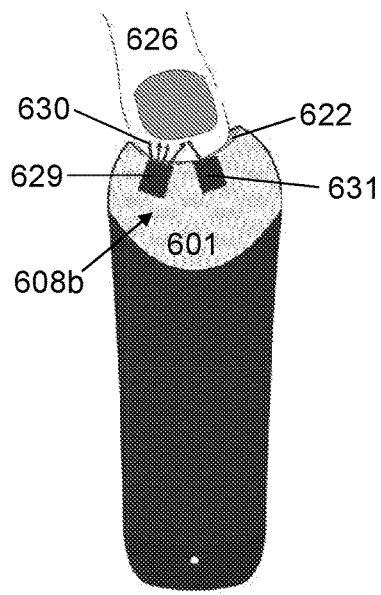
Figure 6B:
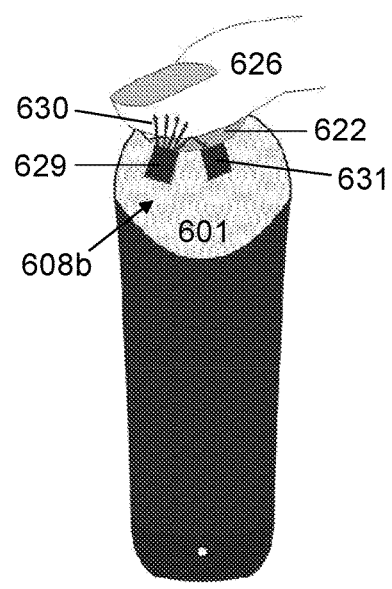

FIGS. 6a and 6b show the relative positioning of the thumb 626 and recess 622 of FIGS. 5a and 5b in greater detail. As shown in these figures, the SPO2 sensor 608b comprises an emitter 629 configured to illuminate the user's thumb 626 with light 630 (e.g. red and/or infrared light) when the thumb 626 is positioned within the concave recess 622, and a detector 631 configured to detect light 630 from the emitter 629 which has been reflected by the user's thumb 626. When the phone 601 is held in the user's left hand, the thumb 626 covers the emitter 629 and detector 631 such that the light 630 enters the thumb 626 and is reflected back onto the detector 631 to allow a measurement of the blood oxygenation. In contrast, when the phone 601 is held in the user's right hand, the thumb 626 does not fully cover the emitter 629 and detector 631. As a result, the detector 631 also receives light 630 directly from the emitter 629 which has not entered the user's thumb 626. This crosstalk between the emitter 629 and detector 631 causes an increase in the detected signal which prevents an accurate reading. Furthermore, if the user's right thumb 626 is so misaligned with the SPO2 sensor 608b that the light 630 cannot be reflected onto the detector 631, then the detected signal will decrease as a result of the small number of photons reaching the detector 631. In view of the above, even if the concave recess 622 does not comprise a longitudinal axis and a short axis (e.g. when the recess 622 has a substantially circular or square shape), the rotational offset and tilt of the SPO2 sensor 608b alone may be sufficient to favour a left-handed hold.

In some cases, this deviation from the expected signal could be used to indicate that the phone 601 is being held incorrectly. For example, the phone 601 may be configured to provide an indication when the amount of light 630 detected by the detector 631 of the SPO2 sensor 608b is outside a predefined range. The indication may be a visual or audible error message.

Another way to increase the accuracy and repeatability of the measurements is to make the phone as easy and as comfortable for the user to hold as possible. Research has shown that a prehensile grip (in which the user's finger wrap around the object and the thumb provides an opposing force) is considered to be the most comfortable way of holding a phone and is often the last grip that elderly and arthritic people can maintain. In this respect, one or both of the size and shape of the phone body may be configured to enable the phone to be held with a prehensile grip.

As can be seen in FIGS. 4b-4d, the phone body may comprise front 432 and rear 433 surfaces configured to form an edge 434 of the phone 401 where they meet one another. For example, the front 432 and rear 433 surfaces may be configured to meet one another at an angle $\alpha$ of no more than 90°. This configuration makes it difficult, or even just uncomfortable, to hold the phone 401 in the fingers alone, and therefore serves to encourage a prehensile grip.

Figure 7:
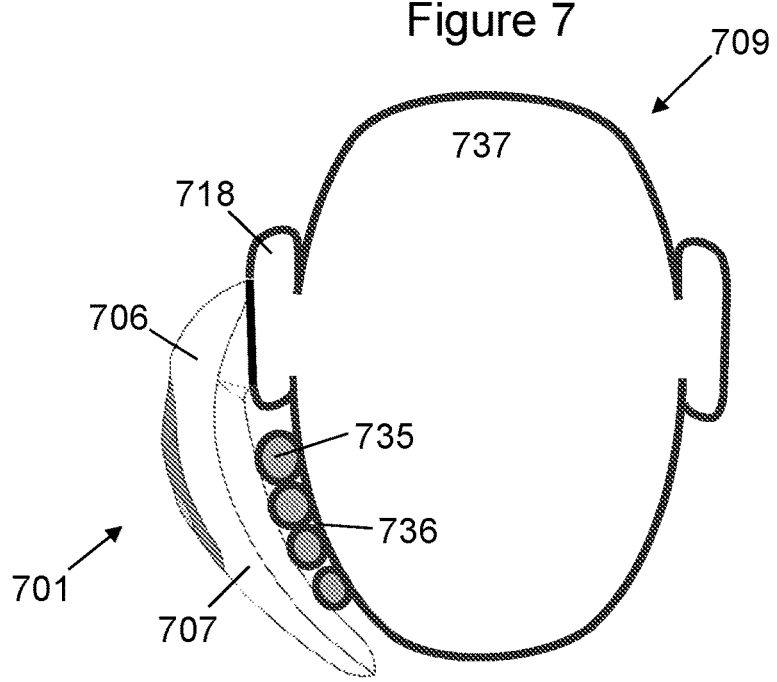
FIG. 7 illustrates schematically a user holding a phone described herein in his/her left hand with a prehensile grip.

FIG. 7 illustrates schematically a user 709 holding a phone 701 described herein in his/her left hand with a prehensile grip. Ideally, the phone 701 should be held as still as possible during ECG measurements in order to reduce the amount of noise picked up by ECG sensor due to muscle movement. To assist with this, one or both of the size and shape of the phone body may be configured to allow the user's fingers 735 to wrap around the phone 701 such that a portion of the fingers 735 is positioned between the phone 701 and the user's cheek 736 when the phone 701 is held in use (as shown). This position creates three points of contact between the phone 701, the user's hand and the user's cheek 736 and is therefore triangulated and stable. The first point of contact is where the earpiece 706 of the phone 701 abuts the user's ear 718, the second point of contact is where the handle 707 abuts the user's fingers 735, and the third point of contact is where the user's fingers 735 abut the user's cheek 736. In this position, any movement of the user's head 737 causes the hand, arm and phone 701 to move as one, thus reducing the noise that would otherwise be created if the phone 701 were able to move relative to the user's ear 718.

Figure 8A:
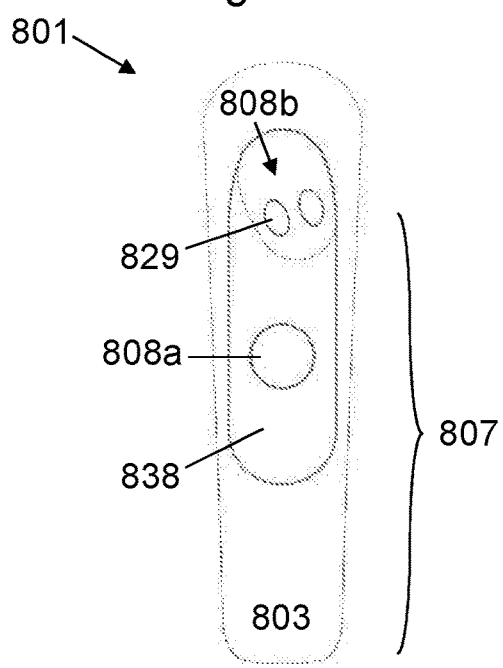
FIG. 8a illustrates schematically one example of a phone described herein comprising a first ECG sensor on the rear side thereof (rear view)
Figure 8B:
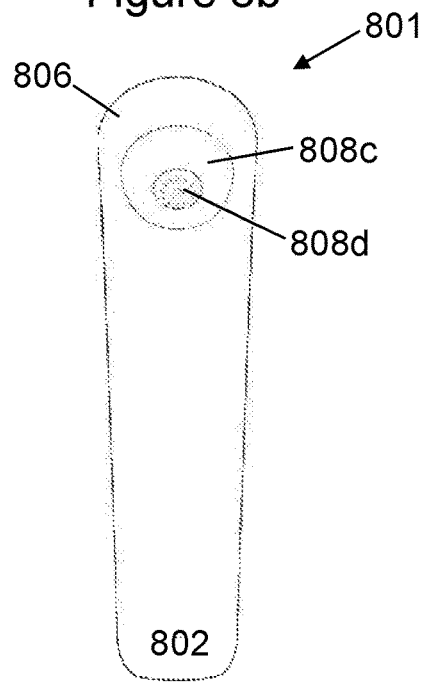
FIG. 8b illustrates schematically one example of a phone described herein comprising a second ECG sensor on the earpiece thereof (front view)

FIGS. 8a and 8b show a further example of the phone 801 described herein in rear view and front view, respectively. In this example, the phone 801 comprises a first ECG electrode 808a positioned on the rear side 803 of the phone body such that the electrode 808a contacts the palm of the user's hand when the phone 801 is held in use. The phone 801 also comprises a second ECG electrode 808c positioned on the earpiece 806 of the phone 801 such that the electrode 808c contacts the ear of the user during use, and an earth electrode 838 positioned on the rear side 803 of the phone body such that the electrode 838 contacts the palm of the user's hand when the phone 801 is held in use. The earth electrode 838 is common to both the first 808a and second 808c ECG electrodes and is configured to ground the user prior to the ECG measurement. When the phone 801 is held as shown in FIG. 7, the pressure exerted by the user's fingers on the front side 802 of the phone 801 presses the rear side 803 of the phone 801 into the palm of the user's hand. The combination of the positioning of the first ECG electrode 808a and the prehensile grip therefore helps to ensure good contact between the user and the first ECG electrode 808a. Furthermore, one or both of the first 808a and second 808c ECG electrodes may have a generally convex shape (e.g. the electrodes 808a,c may be raised by up to 3 mm from the surface of the handle 807/earpiece 806) to facilitate contact with the palm or ear of the user, respectively.

In addition, one or both of the first 808a and second 808c ECG electrodes may comprise metal (possibly in the form of a metal-loaded plastic) on its exterior surface. The use of metal on the exterior surface provides a noticeable temperature difference when the electrode 808a,c touches the user's skin which can serve as a passive indication that the phone is being held correctly. In some cases, the phone may also be configured to provide an active indication when there is insufficient contact between the first ECG electrode 808a and the palm of the user's hand when the phone 801 is held in use.

As also shown in the example of FIG. 8b, the phone 801 comprises a temperature sensor 808d positioned on the earpiece 806 of the phone 801 such that it faces the ear cavity of the user during use. The ear cavity enables reliable temperature readings to be made. Furthermore, in this example, the second ECG electrode 808c has an annular configuration, and the temperature sensor 808d is positioned at the center of the earpiece 806 and encircled by the second ECG electrode 808c. When the temperature sensor 808d is positioned incorrectly, the measured temperature will fall outside of the typical range expected from within the ear cavity. In this way, the temperature measurement provides a further indication of an error in the way the phone 801 is being held. Similar to the SPO2 808b and ECG 808a,c sensors, the phone 801 may be configured to actively alert the user when the temperature measured by the temperature sensor 808d is outside a predefined range.

In some examples, the phone body may comprise one or more markers configured to guide the positioning of the user's hand during use of the phone 801. These markers may comprise at least one of lights, textured regions, coloured regions and demarcations. In one example, the emitter 829 of the SPO2 sensor 808b may be used as a marker. In this scenario, the user would place his/her finger or thumb over the emitter 829 such that no light remained visible.

Figure 9:
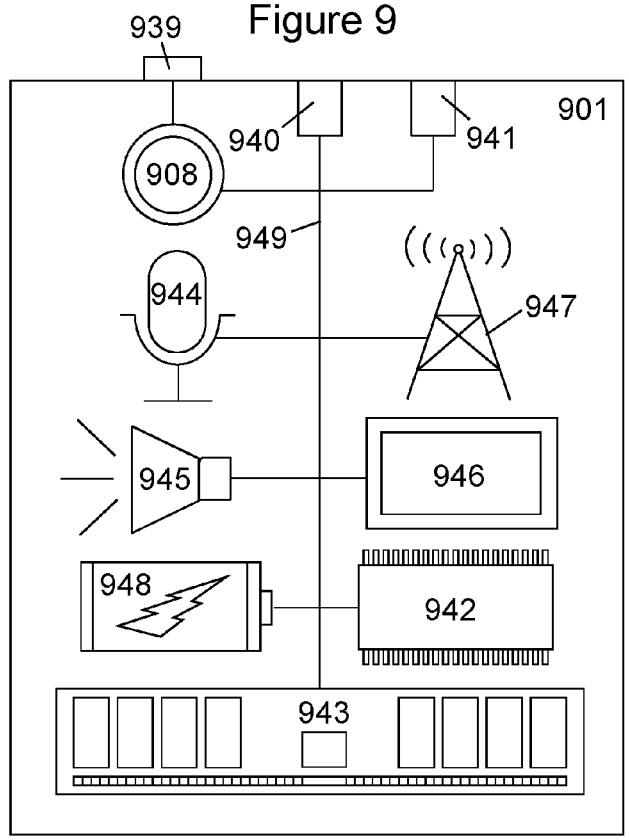
FIG. 9 illustrates schematically another example of a phone described herein.

FIG. 9 shows another example of a phone 901 for use in health monitoring. The phone 901 may be one or more of a wired landline phone, a cordless landline phone, a disposable phone, a mobile phone, a smartphone and a phablet. In the example shown, the phone 901 comprises at least one sensor 908, an initiation button 939, a first dock connector 940, a second dock connector 941, a processor 942, a storage medium 943, a microphone 944, a loudspeaker 945, an electronic display 946, a transceiver 947 and a power source 948, which are electrically connected to one another by a data bus 949.

As described previously, the at least one sensor 908 is configured to measure a vital sign of a user when the phone 901 is held is use, and may comprise one or more of an ECG sensor, an SPO2 sensor, a temperature sensor, and a pulse sensor. The initiation button 939 is configured to initiate measurement of the vital sign by the at least one sensor 908 when pressed.

The first dock connector 940 is configured to enable the vital sign measurement to be uploaded to another device (such as a computer), and may also be configured to enable data (such as configuration settings for the at least one sensor 908) to be downloaded from the other device onto the phone 901. The first dock connector 940 may be a universal serial bus (USB) connector, a mini USB connector or a micro USB connector.

The second dock connector 941 is configured to enable one or more external sensors to be detachably connected to the phone 901, e.g. to increase the number of vital signs that can be measured by the phone 901 or to increase the number of regions of the user's body that can be interrogated at the same time. The second dock connector 941 may be an audio port of the phone 901, such as a single or multiple 2.5 mm, 3.5 mm or 6.35 mm jack.

The processor 942 is configured for general operation of the phone 901 by providing signalling to, and receiving signalling from, the other components to manage their operation. The processor 942 is also configured to convert the vital sign measurement obtained by the at least one sensor 908 into a voice-frequency band signal, such as a DTMF signal. In the case of DTMF, the processor 942 would typically be configured to convert the vital sign measurement into a numeric or alphanumeric code.

The storage medium 943 is configured to store computer code configured to perform, control or enable operation of the phone 901. The storage medium 943 may also be configured to store settings for the other components. The processor 942 may access the storage medium 943 to retrieve the component settings in order to manage the operation of the other components. The storage medium 943 may also be configured to store the vital sign measurement obtained by the at least one sensor 908 with or without the corresponding numeric or alphanumeric code.

In addition, the storage medium 943 may be configured to store predefined thresholds or ranges for one or more sensors 908 or vital signs. In this way, the processor 942 can compare the associated sensor reading (e.g. intensity of illumination) or vital sign measurement (e.g. SPO2 reading) against the predefined threshold or range. The processor 942 may be further configured to generate an indication to alert the user of a potential health issue, or to inform him/her that the phone 901 is being held incorrectly, in the event that the sensor reading or vital sign measurement falls above or below the predefined threshold or outside of the predefined range.

The processor 942 may be a microprocessor, including an Application Specific Integrated Circuit (ASIC). The storage medium 943 may be a temporary storage medium such as a volatile random access memory. On the other hand, the storage medium 943 may be a permanent storage medium such as a hard disk drive, a flash memory, or a non-volatile random access memory.

The microphone 944 and loudspeaker 945 are configured to enable the user to converse with an operator and/or interact with an automated IVR system. In this way, the operator or automated system can request the vital sign measurement from the user, provide step-by-step instructions, guidance or reassurance to the user, and can also answer any questions from the user. When the user is connected to an automated system, the system may comprise voice-recognition software to enable it to interpret any questions or answers from the user.

The electronic display 946 is configured to present the vital sign measurements obtained by the at least one sensor 908 to the user in textual, numeric or graphical form. Additionally or alternatively, the microphone 944 may be configured to present the vital sign measurements to the user in audio form, which could be beneficial to a visually-impaired user. The electronic display 946 may be an LCD, LED or plasma display.

The transceiver 947 is configured to transmit data to, and receive data from, one or more external devices. In particular, the transceiver 947 is configured to transmit the voice-frequency band signal to an operator or automated system for real-time analysis or storage of the corresponding vital sign measurement in a patient health record. The transceiver 947 is also configured to transmit speech from the user to the operator or automated system, and deliver speech from the user or automated system to the user. The transceiver 947 may be a wired or wireless transceiver, and may be configured to transmit and receive data over one or more of a telephone, internet, Bluetooth™ and WiFi™ connection. In some examples, the transceiver 947 may comprise a separate transmitter and receiver.

The power source 948 is configured to provide the other components of the phone 901 with electrical power to enable their functionality. The power source 948 may comprise one or more of a rechargeable battery, a non-rechargeable battery and a mains adapter. When the phone 901 comprises both a battery and a mains adapter, the battery may be configured as a back-up power supply for times when there is a power cut or no access to a mains supply. In addition, when the battery is a chargeable battery, the battery may be charged by the mains supply via the mains adapter.

Figure 10:
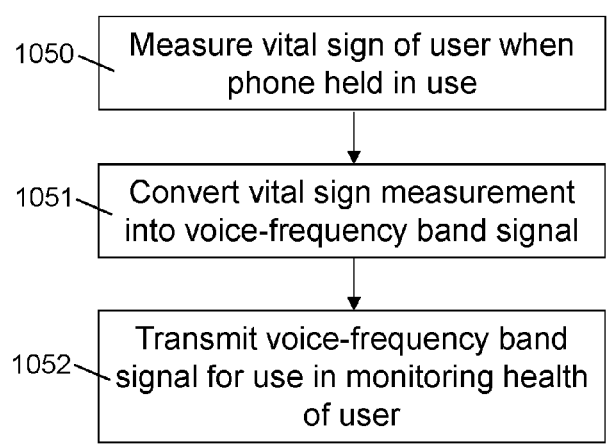
FIG. 10 illustrates schematically the main steps of a method described herein.

FIG. 10 illustrates schematically the main steps 1050-1052 of a method of using a phone described herein. As shown, the method generally comprises: measuring a vital sign of a user when the phone is held in use 1050; converting the vital sign measurement into a voice-frequency band signal 1051; and transmitting the voice-frequency band signal for use in monitoring the health of the user 1052.

Figure 11:
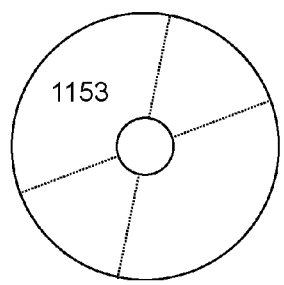
FIG. 11 illustrates schematically a computer-readable medium comprising a computer program configured to perform, control or enable one or more steps of a method described herein.

FIG. 11 illustrates schematically a computer/processor readable medium 1153 providing a computer program. The computer program may comprise computer code configured to perform, control or enable one or more of the method steps 1050-1052 of FIG. 10. In this example, the computer/processor readable medium 1153 is a disc such as a digital versatile disc (DVD) or a compact disc (CD). In other embodiments, the computer/processor readable medium 1153 may be any medium that has been programmed in such a way as to carry out an inventive function. The computer/processor readable medium 1153 may be a removable memory device such as a memory stick or memory card (SD, mini SD, micro SD or nano SD).

The invention claimed is:

1. A phone comprising:
   a phone body defining a handle and an earpiece;
   a pulse oximeter oxygen saturation sensor positioned in a concave recess at least partially on a left side of the handle;
   a first electrocardiogram electrode positioned on the handle;
   a second electrocardiogram electrode positioned on the earpiece; and
   means for transmitting electrocardiography measurements obtained using the first and second electrocardiogram electrodes and photo plethysmography measurements obtained using the pulse oximeter oxygen saturation sensor for use in determining one or more of the pulse transit time and blood pressure of a user based on the electrocardiography and photo plethysmography measurements.

2. The phone of claim 1, wherein the pulse oximeter oxygen saturation sensor comprises an emitter configured to illuminate a thumb or finger of a user with light when the thumb or finger is positioned within the concave recess, and a detector configured to detect light from the emitter which has been reflected by the user's thumb or finger, and wherein the phone is configured to provide an indication when an amount of light detected by the detector of the pulse oximeter oxygen saturation sensor is outside a predefined range.

3. The phone of claim 1, wherein the phone is configured to provide an indication when there is insufficient contact between the first electrocardiogram electrode and a user's hand when the phone is held in use.

4. The phone of claim 1, wherein one or both of the first and second electrocardiogram electrodes have a convex.

5. The phone of claim 1, wherein the phone comprises a temperature sensor positioned on the earpiece, and wherein the temperature sensor is encircled by the second electrocardiogram electrode.

6. The phone of claim 5, wherein the phone is configured to provide an indication when the temperature measured by the temperature sensor is outside a predefined range.

7. The phone of claim 1, wherein the phone body comprises one or more markers configured to guide positioning of a user's hand during use of the phone.

8. The phone of claim 1, wherein the phone comprises an earth electrode positioned on the handle of the phone body, the earth electrode configured to ground a user prior to electrodardiography measurements obtained using the first and second electrocardiogram electrodes.

9. A method of using the phone of claim 1, the method comprising:
   obtaining electrocardiography measurements of a user using the first and second electrocardiogram electrodes, and photo plethysmography measurements of the user using the pulse oximeter oxygen saturation sensor, when the phone is held in use; and
   transmitting the electrocardiography measurements and the photo plethysmography measurements for use in determining one or more of the pulse transit time and blood pressure of the user based on the electrocardiography and photo plethysmography measurements.

10. A non-transitory computer-readable medium comprising computer code configured to perform the method of claim 9.

11. The phone of claim 1, wherein the means for transmitting are configured to transmit the electrocardiography and photo plethysmography measurements as a voice-frequency band signal.

12. A phone comprising:
   a phone body defining a handle and an earpiece;
   a pulse oximeter oxygen saturation sensor positioned in a concave recess at least partially on a left side of the handle;
   a first electrocardiogram electrode positioned on the handle;
   a second electrocardiogram electrode positioned on the earpiece;
   means for determining one or more of the pulse transit time and blood pressure of a user based on electrocardiography measurements obtained using the first and second electrocardiogram electrodes and photo plethysmography measurements obtained using the pulse oximeter oxygen saturation sensor when the phone is held in use; and
   means for transmitting one or more of the pulse transit time and blood pressure for use in monitoring the health of the user.

13. The phone of claim 12, wherein the means for transmitting is configured to transmit one or more of the pulse transit time and blood pressure as a voice-frequency band signal.

14. A method of using the phone of claim 12, the method comprising:
   obtaining electrocardiography measurements of a user using the first and second electrocardiogram electrodes, and photo plethysmography measurements of the user using the pulse oximeter oxygen saturation sensor, when the phone is held in use;

determining one or more of the pulse transit time and blood pressure of the user based on the obtained electrocardiography and photo plethysmography measurements; and transmitting one or more of the pulse transit time and blood pressure for use in monitoring the health of the user.

15. A non-transitory computer-readable medium comprising computer code configured to perform the method of claim 14.

* * * * *